United States Patent [19]

Dickman

[11] 4,423,722

[45] Jan. 3, 1984

[54] BANDAGE GUARD

[76] Inventor: Dennis M. Dickman, 227 Princeton St., Jefferson, Mass. 01522

[21] Appl. No.: 308,094

[22] Filed: Oct. 5, 1981

[51] Int. Cl.³ .................... A61F 13/00; A61D 13/00; B65B 11/00

[52] U.S. Cl. .............................. 128/132 R; 128/165; 2/2; 150/52 R

[58] Field of Search ................ 128/132 R, 153, 87 R, 128/87 A, 138 R, 165; 2/2, 20, 21, 16; 294/25, 131; 132/73; 604/337, 338, 332, 346, 347, 349, 355; 215/12 R, 246, 271, 272, DIG. 6

[56] References Cited

U.S. PATENT DOCUMENTS

| | | | |
|---|---|---|---|
| 1,417,414 | 5/1922 | Sanders | 2/21 |
| 1,634,076 | 9/1928 | Smith | 2/21 |
| 1,753,044 | 4/1930 | Culver | 132/73 |
| 1,879,609 | 9/1932 | Hannon | 132/73 |
| 2,528,456 | 10/1956 | Stevenson | 128/87 R |
| 2,670,736 | 3/1954 | Dunkelberger | 128/132 R |
| 3,403,714 | 10/1968 | Hulm | 150/0.5 |

*Primary Examiner*—Henry J. Recla
*Assistant Examiner*—Karin M. Reichle

[57] ABSTRACT

A bandage guard including a rigid tubular member having an open first end and a closed second end, a flexible sleeve member mounted on the tubular member, the sleeve member having an expandable opening therein, the sleeve member opening being smaller than the tubular member first end.

1 Claim, 2 Drawing Figures

8
10
4
2
8

2
8
10
6
4
8

BANDAGE GUARD

BACKGROUND OF THE INVENTION

1. Field of the Invention

This invention relates to medical dressings and is more particularly directed to a guard for finger bandages.

2. Description of the Prior Art

It has been recognized that protection of a bandaged finger is desirable to permit function of a patient's hand without danger of reinjuring the finger or agitating the wound. A useful device would be one that protects the finger from being struck or bent. A further desirable feature would be a barrier means to prevent wetting of the bandage during showering, and the like. A still further desirable feature in some cases would be the provision of means to prevent impurities reaching the bandage.

Devices of this general type have been shown in the prior art. U.S. Pat. No. 1,417,414, issued May 23, 1922 to L. J. Sanders discloses a finger protector in the form of a cup of "unyielding but not rigid" material, configured to fit over a bandage. U.S. Pat. No. 1,634,076, issued Sept. 11, 1928 to J. M. Smith discloses a digit guard comprising a soft metal unitary member having an end portion from which extend a series of tongues. U.S. Pat. No. 2,528,456, issued Oct. 31, 1950 to T. Stevenson shows a splint of a generally cylindrical shape and of "limitedly flexible" material.

While the devices of the prior art have doubtless proved useful, they fail to provide the desired features enumerated above.

SUMMARY OF THE INVENTION

It is, therefore, an object of the present invention to provide a guard which protects a bandaged finger from being wetted and/or subjected to impure or undesirable substances, and from being struck or bent.

A further object of the invention is to provide such a bandage guard as may be easily slipped on and off a bandaged finger which may or may not have a finger guard, depending upon the nature of the wound, without agitating the wound.

A still further object of the invention is to provide such a bandage guard as is economical to make and safe and easy to use.

With the above and other objects in view, as will hereinafter appear, a feature of the present invention is the provision of a bandage guard comprising a rigid tubular member having an open first end and a closed second end, a flexible sleeve member mounted on the tubular member, the sleeve member having an expandable opening therein, the opening being smaller than the tubular member first end.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention from which its novel features and advantages will be apparent.

DESCRIPTION OF THE PREFERRED EMBODIMENT

Figure 1:
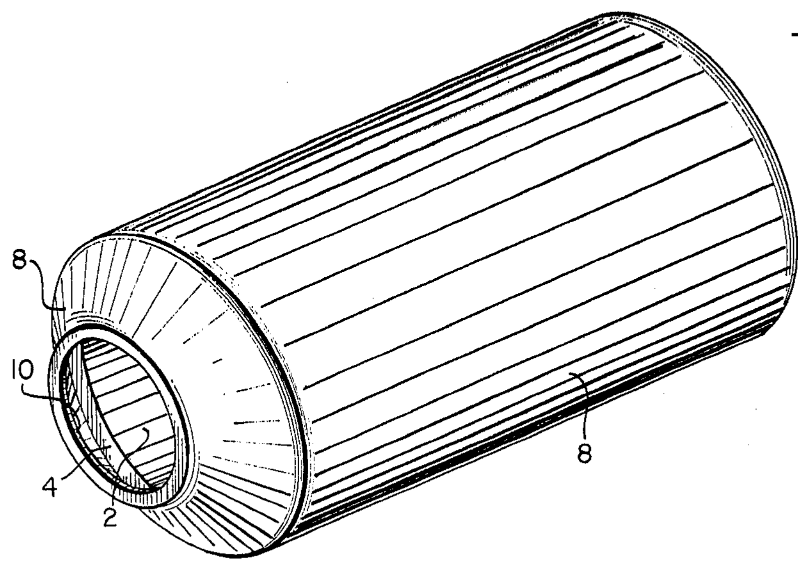
FIG. 1 is a perspective view of one form of guard illustrative of an embodiment of the invention.
Figure 2:
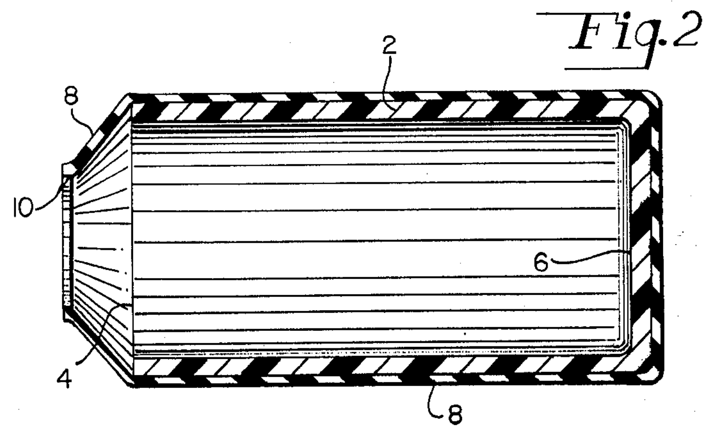
FIG. 2 is a center-line section view thereof.

Referring to the drawings, it will be seen that the illustrative bandage guard includes a rigid tubular member 2, preferably of plastic or metal, having an open first end 4 and a closed second end 6. A flexible sleeve member 8, preferably of plastic or rubber, is fixed to the tubular member 2 and extends from the first end 4 thereof. As illustrated, the sleeve member 8 may encompass the tubular member 2. Alternatively, the sleeve member 8 may be an angular member fixed to the tubular member on the side of the tubular member and extending beyond the open end of the tubular member.

The flexible sleeve member 8 is provided with an opening 10 which is in general alignment with and is smaller than the tubular member open end 4. The opening 10 is biased toward its smallest size, but is expandable to accommodate a finger disposed therein. If the sleeve member is of elastomeric material, the opening 10 will be correspondingly elastic and expandable. If the sleeve material is not elastomeric, a ring of elastomeric material (not shown) may be provided proximate the opening 10.

In a preferred embodiment, the length of the tubular member 2 is about 3 inches and its diameter is about $1\frac{1}{2}$ inches. The sleeve opening 10 is about $\frac{5}{8}$ inch in diameter in its non-expanded state.

In use, a bandaged finger is inserted in the device through the opening 10 which expands to accommodate the finger. The smooth interior of the rigid tubular member permits sliding of the bandage therein without the device tugging on the bandage. Once in place, the tubular member 2 protects the bandaged area from bending or being struck, while the sleeve 8, fitting snugly about the finger, prevents entry of water, dirt or impurities.

It is to be understood that the present invention is by no means limited to the particular construction herein disclosed and/or shown in the drawings, but also comprises any modifications or equivalents within the scope of the disclosure.

Having thus described my invention what I claim as new and desired to secure by Letters Patent of the United States is:

1. A bandage guard comprising a rigid tubular member having an open first end and a closed second end, a flexible sleeve member mounted on said tubular member, said sleeve member being closed at one end, and said tubular member being disposed wholly within said sleeve member, said second end of said tubular member being adjacent said closed end of said sleeve member, said sleeve member extending from said first end of said tubular member in a direction inwardly of said tubular member, said sleeve member having at its end removed from said tubular member an expandable opening therein, said opening being smaller than said tubular member open first end.

* * * * *